(12) United States Patent
Cheung et al.

(10) Patent No.: US 7,247,760 B2
(45) Date of Patent: Jul. 24, 2007

(54) HYDROGENATION PALLADIUM-SILVER CATALYST AND METHODS

(75) Inventors: Tin-Tack Peter Cheung, Kingwood, TX (US); Joseph J. Bergmeister, III, Kingwood, TX (US)

(73) Assignee: Chevron Phillips Chemical Company, The Woodlands, TX (US)

( * ) Notice: Subject to any disclaimer, the term of this patent is extended or adjusted under 35 U.S.C. 154(b) by 67 days.

(21) Appl. No.: 10/457,635

(22) Filed: Jun. 9, 2003

(65) Prior Publication Data

US 2004/0024272 A1 Feb. 5, 2004

Related U.S. Application Data

(60) Provisional application No. 60/388,307, filed on Jun. 14, 2002.

(51) Int. Cl.
| | |
|---|---|
| *B01J 31/00* | (2006.01) |
| *B01J 27/08* | (2006.01) |
| *B01J 27/13* | (2006.01) |
| *C07C 5/05* | (2006.01) |
| *C07C 5/08* | (2006.01) |

(52) U.S. Cl. ............... 585/261; 502/224; 502/226; 502/227; 502/230; 502/231; 502/162; 502/167; 502/200

(58) Field of Classification Search ............... 502/224, 502/226, 227, 230, 231, 162, 167, 200; 585/261
See application file for complete search history.

(56) References Cited

U.S. PATENT DOCUMENTS

| | | | |
|---|---|---|---|
| 2,802,889 A | | 8/1957 | Frevel et al. |
| 3,325,556 A | | 6/1967 | De Rossef et al. |
| 3,679,762 A | * | 7/1972 | La Hue et al. ............. 585/260 |
| 4,113,970 A | | 9/1978 | Tanabe et al. |
| 4,128,595 A | * | 12/1978 | Montgomery ............... 585/261 |
| 4,347,392 A | * | 8/1982 | Cosyns et al. ............. 585/259 |
| 4,404,124 A | | 9/1983 | Johnson et al. |
| 4,484,015 A | | 11/1984 | Johnson et al. |
| 4,571,442 A | * | 2/1986 | Cosyns et al. ............. 585/261 |
| 4,762,956 A | * | 8/1988 | Liu et al. ................... 585/259 |
| 5,059,731 A | | 10/1991 | Berrebi |
| 5,059,732 A | * | 10/1991 | Cosyns et al. ............. 585/259 |
| 5,475,173 A | | 12/1995 | Cheung et al. |
| 5,489,565 A | | 2/1996 | Cheung et al. |
| 5,510,550 A | | 4/1996 | Cheung et al. |
| 5,583,274 A | | 12/1996 | Cheung et al. |
| 5,585,318 A | | 12/1996 | Johnson et al. |
| 5,587,348 A | | 12/1996 | Brown et al. |
| 5,648,576 A | | 7/1997 | Nguyen Than et al. |
| 5,889,187 A | | 3/1999 | Nguyen Than et al. |
| 6,054,409 A | | 4/2000 | Nguyen Thanh et al. |
| 6,096,933 A | | 8/2000 | Cheung et al. |
| 6,127,588 A | | 10/2000 | Kimble et al. |
| 6,350,717 B1 | | 2/2002 | Frenzel et al. |
| 6,417,136 B2 | | 7/2002 | Cheung et al. |
| 6,437,206 B1 | | 8/2002 | Meyer et al. |
| 2001/0001805 A1 | | 5/2001 | Brown et al. |
| 2004/0192982 A1 | * | 9/2004 | Kuechler et al. ........... 585/259 |

FOREIGN PATENT DOCUMENTS

| | | |
|---|---|---|
| EP | 0124744 | 3/1984 |
| EP | 0 722 776 A1 | 1/1996 |
| EP | 0 792 685 A1 | 1/1997 |
| EP | 0689872 | 8/2001 |

OTHER PUBLICATIONS

Y.H. Park et al., "Promotional Effects of Potassiumom Pd/Al2O3 Selective Hydrogenation Catalysts" Ind. Eng. Chem. Res., vol. 31, No. 2, 1992 p. 469–474, no month.

Y.H.Park et al., Potassium Promotor for Palladium on Alumina Selective Hydrogenation Catalysts, J. Chem. Soc. Chem. Common., 1991 p. 1188–1189, no month.

J.P. Botaiux et al., "Newest Hydrogenation Catalysts," Hydrocarb. Process, Mar. 1985, p. 51–59.

\* cited by examiner

*Primary Examiner*—Elizabeth D. Wood
(74) *Attorney, Agent, or Firm*—Rodney B. Carroll; K. KaRan Reed; David W. Dockter

(57) ABSTRACT

A catalyst composition comprising palladium, silver and a support material (preferably alumina) is contacted with a liquid composition comprising an iodide component such as ammonium iodide, and the catalyst is then calcined. An improved process for hydrogenation, especially selectively hydrogenating acetylene (to ethylene), using this improved catalyst composition with improved conversion and deactivation.

53 Claims, No Drawings

HYDROGENATION PALLADIUM-SILVER CATALYST AND METHODS

CROSS REFERENCE TO RELATED APPLICATIONS

This application claims priority to U.S. provisional application Ser. No. 60/388,307, filed on Jun. 14, 2002.

FEDERALLY SPONSORED RESEARCH

Not applicable

REFERENCE TO MICROFICHE APPENDIX

Not applicable

FIELD OF THE INVENTION

This invention relates to novel catalysts and to methods of making supported palladium/silver compositions exhibiting improved hydrogenation catalyst performance. In another aspect, this invention relates to processes for hydrogenation of hydrocarbons generally, and particularly selectively hydrogenating acetylene to ethylene employing supported palladium/silver catalysts having been prepared by the preparation method of this invention.

BACKGROUND OF THE INVENTION

The selective hydrogenation of unsaturated hydrocarbons, and especially the hydrogenation of acetylene which is present as an impurity in mono-olefin-containing streams (e.g., ethylene streams from thermal ethane crackers), is commercially carried out with an alumina-supported palladium/silver catalyst, substantially in accordance with the disclosure in U.S. Pat. No. 4,404,124 and its division, U.S. Pat. No. 4,484,015, the disclosures of both patents being incorporated herein by reference. The operating temperature for this process is selected such that essentially all acetylene is hydrogenated to ethylene while only an insignificant amount of ethylene is hydrogenated to ethane. It is desirable to minimize hydrogenation of ethylene to ethane in order to minimize ethylene losses and to avoid a "runaway" reaction which is difficult to control, as has been pointed out in the above-identified patents. The selective acetylene hydrogenation process can be most effectively controlled when there is a large difference between the temperature at which essentially all acetylene is hydrogenated and a higher temperature at which excessive ethylene-to-ethane conversion occurs.

SUMMARY OF THE INVENTION

In one embodiment, the invention provides an improved palladium-silver catalyst contained on a support, the catalyst having been combined with an iodide component, and then calcined, the catalyst exhibiting good deactivation and selectivity in the hydrogenation of unsaturated hydrocarbons.

In a further aspect of the invention, a preparation method comprises contacting a solid composition (also referred to as "base catalyst composition" or "starting catalyst composition") comprising palladium, silver, and an inorganic support material with a liquid composition containing ammonium iodide, under contacting conditions which are effective in enhancing the selectivity of the solid catalyst composition.

In yet another embodiment, the silver may be contained in the liquid composition rather than in the solid base catalyst composition. The catalyst containing the ammonium iodide is then preferably calcined at an elevated temperature.

Further in accordance with this invention, a process for hydrogenating unsaturated hydrocarbons generally, and for selectively hydrogenating acetylene (preferably present in a small amount in an ethylene-containing gas stream) with hydrogen gas is carried out with a catalyst prepared by the methods described herein.

BRIEF DESCRIPTION OF THE DRAWINGS

None.

DESCRIPTION OF EMBODIMENTS OF THE INVENTION

The catalyst composition of matter of this invention includes: (a) palladium metal and/or at least one palladium compound (preferably palladium oxide), (b) silver metal and/or at least one silver compound (preferably silver oxide), (c) an iodide component, and (d) an inorganic support material selected from the group consisting of alumina, silica, titania, zirconia, aluminosilicates, zinc aluminate, zinc titanate, and mixtures of two or more of these components, preferably alumina, more preferably alpha-alumina. Generally, the catalyst composition comprises between about 0.01 and about 2 weight % Pd, between about 0.01 and about 10 weight % Ag, and the catalyst contains between about 1 and about 10,000 ppm by weight of an iodide component. In one embodiment, the catalyst composition comprises between about 0.01 and about 0.6 wt % Pd, between about 0.02 and about 5 wt % Ag, and between about 10 and about 1000 ppm by weight of an iodide component. In yet another embodiment of the catalyst, the iodide component is present in an amount of between about 15 and about 500 ppm by weight. The catalyst also has an Ag:Pd weight ratio of about 1:1 to about 10:1, more preferably about 5:1 to about 8:1. The catalyst particles can have any suitable shape (spherical, cylindrical, and trilobal and are preferably either spheres or cylindrical extrudates. The catalyst particles can have any suitable particle size, and generally have a size of from about 1 to about 10 mm and preferably about 2-6 mm. The catalyst particles can have any suitable surface area generally ranging between about 1 to about 200 preferably about 10-100 $m^2/g$. Surface areas discussed herein measured by the BET method by Bruhauer, Emmett and Teller employing $N_2$.

The catalyst particles can be prepared by any suitable means. The components (a), (b) and (c) can be deposited onto and/or incorporated into the inorganic support material by any suitable means and in any suitable order. For instance, the iodide can be incorporated into the support material, followed by impregnation of the iodide containing support material with Pd and Ag compounds (such as $H_2PdCl_4$ and $AgNO_3$), sequentially in any order or simultaneously, followed by drying and calcining of the thus-impregnated composition. In an alternative embodiment, a supported palladium catalyst composition, such as a $Pd/Al_2O_3$ composition, which is commercially available, can be impregnated with a silver compound and ammonium iodide, either sequentially in any order or simultaneously, followed by drying and calcining of the thus-impregnated composition.

In some embodiments of the invention, the starting material, also referred to herein as "base catalyst," for preparation of the catalyst of this invention can be any supported palladium- and silver-containing catalyst composition produced as desired by combining silver and palladium on a suitable support. The silver component is generally dispersed substantially homogeneously throughout the catalyst support. The palladium is preferably contained on the surface of the catalyst. This base catalyst composition can be a fresh catalyst or it can be a used catalyst which has been oxidatively regenerated as a catalyst composition. The base catalyst can contain any suitable solid support material as described above. In one embodiment, the palladium/silver/alumina composition described in U.S. Pat. No. 4,404,124, the disclosure of which is incorporated herein by reference, is used.

In accordance with the invention, the starting or base catalyst is contacted with a liquid iodide composition which contains a dissolved iodide component such as, for example, ammonium iodide ($NH_4I$), or elemental iodine ($I_2$) dissolved in water. The liquid iodine composition comprises any solvent that will dissolve the iodide component sufficiently to be used in the method of the invention. The solvent may be water or a polar solvent such as an alcohol, ester, ether or the like containing about 1 to 10 carbons. Water and lower alkyl alcohols are preferred solvents for the iodine component(s). Generally, the concentration of the iodide component in the liquid composition and the weight ratio of iodide component to the base catalyst composition are chosen so as to incorporate sufficient iodide on an elemental basis into the composition to produce an efficient catalyst.

The iodine in the catalyst may be provided by any suitable iodide component which can be dissolved in the liquid and applied to the catalyst. Suitable iodides are ammonium iodide ($NH_4I$), hydrogen iodide (HI), iodine ($I_2$), tetraalkylammonium iodides, and mixtures thereof. Examples of tetraalkylammonium iodides include tetramethylammonium iodide, tetraethylammonium iodide, tetrabutylammonium iodide, methyltriethylammonium iodide. The iodide component is used in the substantial absence of an alkali metal iodide such as potassium iodide. When hydrogen iodide is the iodide component, it may be used as a stable liquid solution, such as, for example, a 57% aqueous solution. Salts of hydrogen iodide may also be used as the iodide component. The liquid iodide composition is chosen so that the final concentration of iodine in the catalyst will be in the desired range of between about 1 to about 10,000 ppm. Suitable iodide concentrations in the liquid composition are in the range of between about 0.001 to 1.0 mmole/cc, preferably about 0.01 to 0.5 mmole/cc, and more preferably about 0.01 and 0.05 mmole/cc of iodide.

In this specification, the terms palladium or silver mean the element palladium or silver, respectively, which can be provided to the composition as a palladium component or silver component, which may be any functional compound, salt or complex of palladium or silver. By the terms iodine is meant elemental iodine which can be provided to the catalyst composition as an iodide component. The iodide component can be any functional compound, salt, complex, or iodine.

If a compound, salt or complex of iodine is used, the cation should be chosen so that the cation does not become a substantial part of the catalyst, that is, the cation would be eliminated during calcining. Thus, the catalyst composition after calcining would have a substantial absence of deleterious cations such as alkali metals such as potassium and sodium.

The contacting of the supported Pd/Ag base catalyst composition with the liquid iodide $NH_4I$ composition can be carried out in any suitable manner. In general, the catalyst composition and the liquid iodide composition are contacted or mixed for a time period of at least about 1 second, preferably about 10 seconds to about 10 hours, generally at ambient temperatures, e.g., about 60° to about 90° F., (16° to 32° C.). More preferably, the time period is about 0.02 to about 2 hours, and the temperature is in the range of about 70° to about 85° F. (21° to 30° C.). The contacting pressure is not a critical variable and generally can be any pressure in the range of from below atmospheric to more than 100 psig. Due to economic considerations, the pressure during the contacting step may be approximately atmospheric, for instance, from about 10 psig to about 25 psig. In performing the contacting step, the temperature should be below the boiling point of the liquid and the contacting step should be carried out to suitably provide the desired catalyst. This contacting step can be carried out as a batch-type operation such as, mixing, soaking, spraying, or by incipient wetness) or continuously (for example, by using a mixing screw or a static mixer equipped with internal baffles or by spraying the base catalyst composition which is placed on a moving conveyer belt with the aqueous composition).

If necessary, the catalyst composition is then separated from the water composition by any conventional solid-liquid separation technique, such as filtering, decanting of the liquid, centrifuging, and the like. This separation step may only be required if the contacting step involved soaking. Thereafter, the catalyst composition is dried, generally for a time period of between about 0.2 and about 20 hours, preferably between about 2 and about 6 hours), at a temperature of about 100° F. to about 300° F. (38° to 149° C.), preferably between about 200° and about 266° F. (94° to 130° C.). It is preferred to then heat, or calcine the dried catalyst composition, generally for a time period of about 0.2-20 hours, preferably between about 1 and about 6 hours at a temperature of between about 575° and about 1300° F. (300° to 705° C.), preferably about 750° to between about 1100° F. (398° and 593° C.). Both the drying step and the calcining step can be carried out in an oxidizing atmosphere or in an inert gas atmosphere (e.g., under $N_2$, He, Ar, and the like), and is preferably carried out in air.

In a further embodiment, the catalyst of this invention can be prepared from the components without use of a base catalyst. In this method, the selected inorganic support (e.g., alumina), is first contacted with the palladium component to impregnate the support with the palladium. In this procedure, a palladium compound contained in a liquid composition (preferably water) is impregnated into the selected support, preferably by soaking. The palladium component can be any compound, complex or salt of palladium which is effective to impregnate the support. Suitable palladium compounds include palladium chloride, palladium bromide, palladium nitrate, palladium oxide, and palladium sulfate. Sufficient palladium compound is used so that the catalyst will contain between about 0.01 to about 2 wt % Pd. After impregnation, the support is dried and then calcined by heating at temperatures in the range of from about 575 to about 1300° F. (300° and 705° C.) for about 0.2 to about 20 hours.

The resulting calcined intermediate is then contacted as by soaking or immersion in a liquid composition (preferably water) of a silver compound, salt or complex to impregnate the support with silver. Suitable silver compounds include silver nitrate, silver chloride, silver iodide, silver oxide, and silver sulfate. Sufficient silver compound is used so that the catalyst will contain between about 0.01 to about 10 wt % Ag. After impregnation with the silver compound, the support is then dried and again calcined under the same conditions to form the base catalyst comprising the inorganic support impregnated with Pd and Ag.

The resulting calcined intermediate is then contacted with the iodide component in the amounts and under the conditions described herein. The iodide impregnated base catalyst is then dried and calcined as described above to provide the catalyst of the invention.

It will be understood that the final calcining step will be effective to eliminate the nitrogen from the composition as well as a substantial portion of the iodine introduced by the iodide impregnation. In general, up to 50 wt %, up to 75 wt % or even up to 90 wt % of the iodine may be eliminated during the calcining step. Therefore, the catalyst should be impregnated with a liquid composition containing sufficient iodide so as to have a residual iodine on the support in the amount of about 1 to 10,000 ppm, preferably about 10 to 10,000 ppm iodine, measured as elemental iodine by Neutron Activation Analysis.

It will also be understood that the catalyst of the invention is not made with alkali metal components so that the catalyst has a substantial absence of any alkali metal iodide such as KI.

The thus-prepared catalyst composition which has been dried and, optionally, calcined, can then be employed in the hydrogenation of unsaturated hydrocarbons. According to a preferred embodiment, the catalyst is used in a process for hydrogenating acetylene to primarily ethylene. Optionally, the catalyst is first contacted, prior to the acetylene hydrogenation, with hydrogen gas or with a gaseous hydrocarbon generally at a temperature in the range of about 60° F. to about 800° F. (15° to 426° C.), preferably about 200° to about 600° F. (93° to 315° C.), more preferably about 300° to about 500° F. (149° to 260° C.), and most preferably at about 400° F. (204° C.) for a time period of about 0.5 to about 20 hours. During this contacting with $H_2$ or hydrocarbon(s) before the selective acetylene hydrogenation commences, palladium and silver compounds (primarily oxides) which may be present in the catalyst composition after the drying step and the optional calcining step (described above) are substantially reduced to palladium and silver metal. When this optional reducing step is not carried out, the hydrogen gas present in the reaction mixture accomplishes this reduction of oxides of Pd and Ag during the initial phase of the acetylene hydrogenation reaction of this invention.

The catalyst compositions of the invention have superior selectivity and conversion rates and lower deactivation rates. By deactivation rate is meant the decrease in percent conversion in a given time frame or period. The percent conversion is defined as the percent of acetylene that is hydrogenated to ethane and ethylene, or oligomerized to butenes and heavy hydrocarbons. The catalysts of the invention provide excellent results in hydrogenation of unsaturated hydrocarbons generally, and especially in the selective hydrogenation of acetylene.

The hydrogenation process of this invention can be carried out by contacting a fluid which comprises a highly unsaturated hydrocarbon, in the presence of hydrogen with a catalyst composition described above. Preferably the fluid containing a highly unsaturated hydrocarbon contains an unsaturated alkene stream containing an alkyne, a diolefin, or both as an impurity, generally at a level of about 1 mg/Kg (ppm) to about 50,000 ppm of the fluid. The unsaturated alkene in the fluid can be ethylene, propylene, butenes, or combinations of two or more thereof. The highly unsaturated hydrocarbon can be, for example, an alkyne, a diolefin, or combinations of any two or more thereof. Examples of suitable alkynes include, but are not limited to, acetylene, propyne, 1-butyne, 2-butyne, 1-heptyne, phenylacetylene, 1-octyne, 1-nonyne, 1-decyne, and mixtures of two or more thereof. The preferred alkyne is acetylene. These alkynes are primarily hydrogenated to propylene, and butynes (1-butyne, 2-butyne) are primarily hydrogenated to the corresponding alkenes. For example, acetylene is primarily hydrogenated to ethylene, propyne is primarily hydrogenated to propylene, and butynes (1-butyne, 2-butyne) are primarily hydrogenated to the corresponding butenes (1-butene, 2-butenes). Similarly, in the selective hydrogenation of diolefins, the diolefins are hydrogenated to the corresponding monoolefins such as, for example, 1,3-butadiene is hydrogenated to butenes and pentadienes are selectively hydrogenated to pentenes.

Non-limiting examples of suitable diolefins, preferably containing 3-12 carbon atoms per molecule which can be hydrogenated in the process of this invention include propadiene, 1,2-butadiene, 1,3-butadiene, isoprene, 1,2-pentadiene, 1,3-pentadiene, 1,4-pentadiene, 1,2-hexadiene, 1,3-hexadiene, 1,4-hexadiene, 1,5-hexadiene, 2-methyl-1,2-pentadiene, 2,3-dimethyl-1,3-butadiene, heptadienes, methylhexadienes, octadienes, methylheptadienes, etc.

The highly unsaturated hydrocarbon-containing fluid feed for the hydrogenation process of this invention can also comprise other hydrocarbons, in particular, monoolefins and aromatic hydrocarbons which can be present in the feed at a level of at least 30 volume % include, but are not limited to, ethylene, propylene, 1-butene, 2-butene, isobutylene.

The fluid feed which may be liquid or gaseous at the hydrogenating conditions of this process generally comprises about 0.1 to about 99.9 weight % of at least one olefin. The fluid feed can additionally comprise other hydrocarbons (at a level of about 0.1-99.9 weight %), in particular diolefins, aromatic hydrocarbons, such as benzene, toluene, styrene and ethylbenzene, which may be present at a level of about 50-99 weight %. However, it is within the scope of this invention to employ feeds which contain about 100% of at least one diolefin, such as substantially pure dicyclopentadiene. Also, the feed may contain small amounts, generally less than about 0.05 weight %, particularly from about 10 to about 400 ppm, of sulfur compounds, as impurities. Suitable sulfur compounds include, for example, $H_2S$, carbonyl sulfide, carbon disulfide, mercaptans, organic sulfides such as thiophene, organic di-, tri- and tetrasulfides. Carbon monoxide and/or water (generally less than about 0.05 mole % of each) may also be present as impurities.

The selective hydrogenation process of this invention is generally carried out by contacting a feed stream containing at least one highly unsaturated hydrocarbon and molecular hydrogen with the catalyst of this invention which may be contained in a fixed bed. Generally, from about 1 to about 10, preferably from about 1 to about 2, moles of hydrogen are employed for each mole of the highly unsaturated hydrocarbon present in the feed. The temperature necessary for the selective hydrogenation process of this invention depends largely upon the activity of the catalyst and the desired extent of hydrogenation. Generally, reaction temperatures in the range of from about 50° F. (10° C.) to about 550° F. (287° C.), preferably about 65° F. (18° C.) to about 475° F. (245° C.), and most preferably 85° F. (300° C.) to 400° F. (204° C.) can be used. A suitable reaction pressure generally is in the range of from about 15 to about 2,000 pounds per square inch gauge (psig), preferably from 50 to about 1,500 psig, and most preferably from about 100 to about 1,000 psig. The liquid hourly space velocity (LHSV) of the hydrocarbon feed can vary over a wide range. Typically, the space velocity of the feed will be in the range of from about 0.5 to about 100 liters of hydrocarbon feed per liter of catalyst per hour, more preferably from about 2 to about 60 liters/liter/hour. The hydrogenation process conditions should be such as to avoid significant hydrogenation of monoolefins which are formed by hydrogenation of the highly unsaturated hydrocarbons being initially present in the feed to saturate hydrocarbons such as alkanes and cycloalkanes.

The selective acetylene hydrogenation process of this invention is carried out by contacting (a) a feed gas which comprises acetylene, preferably an ethylene stream containing acetylene as an impurity (generally at a level of about 1 ppm to about 50,000 ppm $C_2H_2$) and (b) hydrogen gas with (c) the catalyst composition(s) of the present invention. In general such feed compositions comprise between about 0.5 to about 1.5 weight % acetylene, from about 8 to about 20 weight % methane, from about 0.1 to about 0.3 weight % hydrogen, and the balance ethylene. In order to best attain substantially complete removal of the acetylene, there should be at least one mole of hydrogen for each mole of acetylene present. Gases (a) and (b) may be premixed before their contact with the catalyst composition (c). It is within the scope of this invention to have additional gases, including, for example, as methane, ethane, propane, propene, butane, butenes, carbon monoxide, hydrogen sulfide, present in the feed gas, as long as they do not significantly interfere with the selective hydrogenation of acetylene to ethylene. Generally, CO and $H_2S$ are present in trace amounts (preferably less than about 0.5 weight percent CO and less than about 50 ppm $H_2S$).

The temperature at which the selective hydrogenation of acetylene to ethylene is carried out in the invention depends largely upon the activity of the catalysts and the extent of acetylene removal desired. Generally, temperatures in the range of from about 60° F. (15° C.) to about 300° F. (148° C.), preferably from about 80° F. (27° C.) to about 250° F. (121° C.), and most preferably from about 100° F. (38° C.) to about 250° F. (121° C.) are used. Any suitable reaction pressure can be employed. Generally, the total pressure is in the range of about 100 to about 1,000 pounds per square inch gauge (psig). The gas hourly space velocity (GHSV) can also vary over a wide range. Typically, the space velocity will be in the range of about 1,000 to about 10,000 $m^3$ of feed per $m^3$ of catalyst per hour, more preferably about 2,000 to about 8,000 $m^3/m^3$/hour.

Regeneration of the catalyst composition can be accomplished by heating the catalyst composition in air, at a temperature which preferably does not exceed about 1300° F. (704° C.) to burn off any organic matter and/or char that has been accumulated on the catalyst composition. Optionally, the oxidatively regenerated composition is reduced with $H_2$ or a suitable hydrocarbon (as has been described above) before its redeployment in the selective hydrogenation of acetylene. It is also within the scope of this invention to treat the oxidatively regenerated catalyst composition with a drying step and an optional calcining step, i.e., in accordance with the method of this invention before the catalyst is redeployed in the selective hydrogenation of acetylene either directly or after reduction with $H_2$ or a suitable hydrocarbon, as has been described above.

The following examples are presented to further illustrate this invention and are not to be construed as limiting its scope.

The following examples illustrate the preparation of supported palladium-silver catalyst by impregnation with a dissolved $NH_4I$ and the use of this catalyst for the selective hydrogenation of acetylene to ethylene as shown in the Table below.

EXAMPLES

In the following examples, Catalyst A of Comparative Examples 4-6 was prepared as described in U.S. Pat. No. 4,484,015. This catalyst contained 0.04 wt % palladium and 0.04 wt % silver on an aluminum oxide support (7/32"×7/32" pellets) with surface area of 5 $m^2$/g. Catalyst B was prepared by impregnating catalyst A with $NH_4I$ in distilled water as described in Examples 1-3. This solution was then added dropwise to catalyst A. After all the $NH_4I$ solution was added to the Catalyst A, the pellets were thoroughly mixed. The wet pellets were then transferred to a dish and dried and calcined as described in Examples 1-3.

Example 1

Preparation of Pd/Ag/$NH_4I$ Catalyst

About 0.128 gm $NH_4I$ was dissolved in about 30.04 gms distilled water. Then using this solution, 100.05 gms. of a Pd/Ag/Alumina base catalyst (Catalyst B) were impregnated. After impregnation, the catalyst was dried at 120° C. (248° F.) and then calcined at 538° C. (1000° F.) for 3 hours.

Neutron Activation Analysis shows that the catalyst contains 30.8 ppm Iodine.

Example 2

Preparation of Pd/Ag/$NH_4I$ Catalyst 0.0301 gm $NH_4I$ were dissolved in 7.60 gm of water. Then 25.05 gm of the Pd/Ag/Alumina Catalyst B were impregnated with the $NH_4I$ solution. The catalyst was then calcined at 539° C. (1002° F.) for 3 hours, and cooled to room temperature in the furnace.

Example 3

Preparation of Pd/Ag/$NH_4I$ Catalyst 0.0660 gms $NH_4I$ were dissolved in 29.9 gms of $H_2O$ to form an impregnation solution. 100.0 gms of Pd/Ag/Alumina Catalyst B were then impregnated with this $NH_4I$ solution. The catalyst was then dried at a temperature of 120° C. (248° F.) for 1 hour. The dried catalyst was then calcined in a furnace at 538° C. (1000° F.) for 3 hours after slowly ramping the temperature up to 220° C. (448° F.) and then to 400° C. (752° F.) at a rate of 5° C. (41° F.)/minute. Neutron Activation Analysis shows that the catalyst contains 54.5 ppm Iodine.

The following examples illustrate the preparation of comparative catalysts which contain potassium iodide (Examples 4-5) or ammonium fluoride (Example 6) as the impregnating composition.

Comparative Example 4

Preparation of Pd/KI Catalyst 0.29 gm potassium iodide were dissolved in 64.01 gm of $H_2O$ to form an impregnation solution. Thereafter 99.99 gms of a Pd containing catalyst having 0.04 wt % palladium were then impregnated with the KI solution. The resulting catalyst contained 32.06 of the KI solution. The catalyst was then dried at 120° C. (248° F.) for 1 hour, followed by calcining at 538° C. (1000° F.) for 3 hours, which included ramping the temperature up at a rate of 5° C. (41° F.)/minute.

Comparative Example 5

Preparation of Pd/Ag/KI Catalyst 100.04 gm of the Pd/Ag/Alumina Catalyst A were impregnated with the remainder (~32 gms) of the KI solution prepared in Example 4. The catalyst was then dried at 120° C. (248° F.) for 1 hour. The catalyst was then calcined at 538° C. (1000° F.) for 3 hours which included ramping the temperature up at the rate of 5° C. (41° F.)/minute.

Comparative Example 6

Preparation of Pd/Ag/NH$_4$F Catalyst 0.235 gm of NH$_4$F were dissolved in 7.45 grams of water to form the impregnation solution. Then 24.97 gm of Pd/Ag/Alumina Catalyst A were impregnated with the solution. The catalyst was then dried at 120° C. and calcined at 400° C. (752° F.) for 3 hours.

In these experiments, the catalysts of the examples were tested in the hydrogenation of acetylene contained in a back-end feed which contained 1.2 to 1.3 weight % acetylene, 13 weight % methane, 0.2 weight % hydrogen with the balance ethylene. Experimental conditions included the reduction pretreatment of 20 grams of each catalyst diluted with 40 grams of Alundum (inert Al$_2$O$_3$) placed in a jacket reactor of inside diameter of 0.652 inch. The process comprised reducing the feed at 400° F. (204° C.) for two hours with 200 ml/min. hydrogen flow at atmospheric pressure. A 2:1 molar ratio of hydrogen to acetylene was used.

The following Table demonstrates use of the catalysts of Examples 1,2, and 3 of the invention in the selective hydrogenation of acetylene contained in an ethylene stream. The catalysts of Comparative Examples 4, 5 and 6 were also included as test catalysts under the same conditions. An untreated catalyst was also tested under the same reaction conditions.

TABLE

| Catalyst Composition | Catalyst Number | Run Number | deactivation rate loss in % conversion/hr | wt % gained/day** | hours on stream | Temperature *(F.) |
|---|---|---|---|---|---|---|
| Pd—Ag—NH$_4$I | EX 1 | 1 | 0.006 | 0.059 | 418 | 140 |
| Pd—Ag—NH$_4$I | Ex 2 | 2 | 0.002 | 0.135 | 257 | 120 |
| PD—Ag—NH$_4$I | EX 3 | 3 | 0.069 | 0.063 | 425.0 | 104 |
| Pd—Ag (G83C) | Commercial | 4 | 1.14565 | 0.4 | 138 | 66-72 |
| Pd—KI | EX 4 | 5 | 0.194 | 0.51 | 308 | 53 |
| Pd—Ag—KI | EX 5 | 6 | 0.621 | 0.085 | 286 | 94 |
|  |  |  | 1.455 |  |  | 94 |
|  |  |  | 0.232 |  |  | 120 |
| Pd—Ag—NH$_4$F | EX 6 | 7 | 0.314 | 1.05 | 120 | 68 |

*Temperature at which the deactivation rate was measured.
**Green oil make deposits on the catalyst which measures weight gain. The green oil make is measured as the weight gained by the catalyst after the experiment divided by the run length of experiment.

As shown in the Table, the catalysts of the invention showed significantly improved deactivation rates as measured by loss in percent conversion per hour. Good selectivity rates were also observed. The table shows that the Deactivation Rates are lower for the processes using the catalysts of the invention than the control catalysts EX. 4-7, even though the temperatures were higher. This is unexpected as one would expect that the use of higher temperatures would result in higher deactivation rates.

The invention has been described with reference to certain preferred embodiments. However, as obvious variations thereon will become apparent to those of skill in the art, the invention is not to be limited thereto.

What is claimed is:

1. A catalyst composition comprising a mixture that has been calcined wherein the mixture comprises at least one palladium component, a silver component, an inorganic support material, and an iodine component selected from the group consisting of ammonium iodide, hydrogen iodide, iodine, and mixtures thereof.

2. The catalyst composition of claim 1, wherein the catalyst composition has a palladium content of about 0.01 to about 2 wt %, a silver content of about 0.01 to about 10 wt %, and an iodine content of about 1 to about 10,000 ppm.

3. The catalyst composition of claim 1, wherein the inorganic support material is selected from the group consisting of alumina, silica, titania, zirconia, aluminosilicates, zinc aluminate, zinc titanate, and mixtures thereof.

4. The catalyst composition of claim 1, wherein the catalyst composition has a palladium content of about 0.01 to about 0.6 wt %, a silver content of about 0.02 to about 5 wt % and, an iodine content of about 10 to about 1000 ppm.

5. The catalyst composition of claim 1, wherein the mixture has been calcined at a temperature of about 575° F. (300° C.) to about 1300° F. (704° C.).

6. The catalyst composition of claim 1 wherein the mixture is heated for a period of from about 0.2 to about 20.0 hours.

7. The catalyst composition of claim 1 wherein at least one palladium component is selected from the group consisting of palladium metal and palladium oxide.

8. The catalyst of claim 1, wherein the iodine component is ammonium iodide.

9. The catalyst of claim 1, wherein the iodine component is iodine.

10. The catalyst composition of claim 7, wherein the catalyst composition has a palladium content of about 0.01 to about 2 wt %, a silver content of about 0.01 to about 10 wt %, and an iodine content of about 1 to about 10,000 ppm; and wherein the inorganic support material is selected from the group consisting of alumina, silica, titania, zirconia, aluminosilicates, zinc aluminate, zinc titanate, and mixtures thereof.

11. The catalyst composition of claim 7, wherein the palladium content is about 0.01 to about 0.6 wt %, the silver content is about 0.02 to about 5, and the iodine content to about 10 to about 1000 ppm.

12. A composition prepared by a method comprising the steps of: contacting a starting material comprising a palladium component, a silver component, and an inorganic support material with a solution comprising an iodine component selected from the group consisting of ammonium iodide, hydrogen iodide, iodine, and mixtures thereof, to provide an iodine-contacted starting material, and calcining said iodine-contacted starting material.

13. The composition of claim 12, wherein the inorganic support material is selected from the group consisting of alumina, silica, titania, zirconia, aluminosilicates, zinc aluminate, zinc titanate, and mixtures.

14. The composition of claim 12, wherein the iodine component is dissolved in a solvent selected from the group consisting of water and polar solvents to form the solution.

15. The composition of claim 12, wherein the support material is alumina, and the iodine component is ammonium iodide dissolved in water.

16. A composition according to claim 12, wherein calcining is carried out at a temperature of about 575° F. (300° C.) to about 1300° F. (704° C.).

17. A catalyst composition comprising at least one palladium component, at least one silver component, an iodine component selected from the group consisting of ammonium iodide, hydrogen iodide, iodine, and mixtures thereof, and an inorganic support material.

18. The catalyst composition of claim 17 which has a substantial absence of alkali metal halide.

19. The composition of claim 12, wherein the iodine component is ammonium iodide.

20. The composition of claim 12 wherein the iodine component is elemental iodine dissolved in water.

21. The catalyst composition of claim 17, wherein the palladium component is palladium metal, palladium oxide, or mixtures thereof.

22. The catalyst composition of claim 17, wherein the composition has a palladium content is about 0.01 to about 2 wt %, a silver content about 0.01 to about 10 wt %, and an iodine content of about 1 to about 10,000 ppm.

23. The catalyst composition of claim 17, wherein the inorganic support material is selected from the group consisting of alumina, silica, titania, zirconia, aluminosilicates, zinc aluminate, zinc titanate, and mixtures thereof.

24. The catalyst composition in accordance with claim 17, wherein the palladium content is about 0.01 to about 0.6 wt %, the silver content is about 0.02 to about 5 wt % Ag, the elemental iodine content is about 10 to 1000 ppm, and the inorganic support material is selected from the group consisting of alumina, titania, zirconia and mixtures thereof.

25. The catalyst composition of claim 17, wherein the catalyst composition has been calcined.

26. The catalyst composition of claim 25, wherein the catalyst composition has been dried prior to calcination.

27. The catalyst composition of claim 25, wherein the composition has been calcined at a temperature of about 575° F. (300° C.) to about 1300° F. (704° C.).

28. A composition prepared by a method comprising the steps of: impregnating a starting material comprising palladium, silver and at least one inorganic support material with a solution comprising an iodine component, and calcining the impregnated starting material at a temperature of about 575° F. (300° C.) to about 1300° F. (704° C.) for a time period of about 0.2 to about 20 hours wherein the iodine component is selected from the group consisting or ammonium iodide, hydrogen iodide, iodine, and mixtures thereof.

29. The composition of claim 28, wherein the iodine component is ammonium iodide.

30. A method for the manufacture of a catalyst composition which comprises the steps of:
(1) contacting (a) a solid composition comprising palladium, silver and an inorganic support material with (b) a liquid composition comprising an iodine component for a time period of at least about 1 second, so as to produce a contacted solid composition, wherein the iodine component is selected from the group consisting of ammonium iodide, hydrogen iodide, iodine, and mixtures thereof; and
(2) calcining the contacted solid composition obtained in step (1).

31. A method according to claim 30, wherein the method is carried out in the substantial absence of potassium iodide.

32. A method in accordance with claim 30, wherein the inorganic support material is selected from the group consisting of alumina, silica, titania, zirconia, aluminosilicates, zinc aluminate, zinc titanate, and mixtures thereof; the liquid composition is water or a polar solvent; and the time period is in the range of from about 10 seconds to about 10 hours.

33. The method of claim 30, wherein the inorganic support material is alumina, and the solid composition contains about 0.01 to about 2.0 wt % palladium and about 0.2 to about 10 wt % silver.

34. The method of claim 30, wherein the iodine component is provided in sufficient amounts to provide iodine present in the catalyst in an amount in the range of from about 1 to about 10,000 ppm.

35. The method of claim 30, wherein the calcining step is conducted at a temperature in the range of from about 575° F. (300° C.) to about 1300° F. (700° C.).

36. The composition prepared by the method of claim 30.

37. The composition prepared by the method of claim 30, wherein the iodine component is ammonium iodide.

38. The method of claim 30, wherein the iodine component is ammonium iodide.

39. A method for the manufacture of a catalyst composition which comprises:
(1) contacting an inorganic support material with a palladium component and calcining the palladium-contacted inorganic support material;
(2) contacting the calcined palladium-contacted inorganic support material with a silver component, and calcining the silver-contacted, palladium-contacted inorganic support material; and
(3) contacting the calcined silver-contacted, palladium-contacted inorganic support material with an iodine component, wherein the iodine component is selected from the group consisting of ammonium iodide, hydrogen iodide, iodine, and mixtures thereof, and calcining the iodine-contacted, silver-contacted, palladium contacted inorganic support material to form the catalyst composition.

40. The method of claim 39, wherein the method is carried out in the substantial absence of potassium iodide.

41. The method of claim 39, wherein the inorganic support material is selected from the group consisting of alumina, silica, titania, zirconia, aluminosilicates, zinc aluminate, zinc titanate, and mixtures thereof.

42. The method of claim 39, wherein each contacting step is carried out by impregnation of the inorganic support material.

43. The method of claim 39, wherein the iodine contacting step is carried out by dissolving an iodine component in water or a polar solvent to form a solution and impregnating the inorganic support material with the solution for a time period of from about 10 seconds to about 10 hours.

44. The method of claim 39, wherein sufficient palladium and silver are used so that the inorganic support material contains about 0.01 to about 2.0 wt % palladium and about 0.2 to about 10 wt % silver.

45. The method of claim 44, wherein the iodine component is provided in sufficient amounts to provide iodine present in the catalyst in an amount in the range of from about 1 to about 10,000 ppm.

46. The method of claim 39, wherein each calcining step is conducted at a temperature in the range of from about 575° F. (300° C.) to about 1300° F. (700° C.).

47. The composition prepared by the method of claim 39.

48. The method of claim 39, wherein the iodine component is ammonium iodide.

49. A process for the hydrogenation of an unsaturated hydrocarbon which comprises contacting an unsaturated hydrocarbon with hydrogen in the presence of the catalyst of claim 1.

50. A process for selectively hydrogenating at least one alkyne containing from 2 to about 8 carbon atoms per molecule which is present in a feed with hydrogen gas, to at least one corresponding alkene containing from 2 to about 8 carbon atoms per molecule, comprising the steps of contacting said feed and said hydrogen gas with the catalyst of claim 1.

51. The process of claim 50, wherein the at least one alkyne is selected from the group consisting of acetylene, propyne, butyne-1 and butyne-2, and mixtures thereof.

52. The process of claim 50, wherein the at least one alkyne is acetylene and the at least one alkene is ethylene.

53. The process of claim 50, wherein the feed contains at least one sulfur compound selected from the group consisting of hydrogen sulfide, carbonyl sulfide and mercaptans.

* * * * *